United States Patent
Park et al.

(10) Patent No.: US 8,518,642 B2
(45) Date of Patent: Aug. 27, 2013

(54) METHOD OF ANALYZING PROBE NUCLEIC ACID, MICROARRAY AND KIT FOR THE SAME

(75) Inventors: Kyung-hee Park, Seoul (KR); Myo-yong Lee, Suwon-si (KR); Kyu-sang Lee, Ulsan (KR); Jong-suk Chung, Hwaseong-si (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 116 days.

(21) Appl. No.: 12/684,345

(22) Filed: Jan. 8, 2010

(65) Prior Publication Data

US 2010/0190651 A1 Jul. 29, 2010

(51) Int. Cl.
- *C12Q 1/68* (2006.01)
- *C12P 19/34* (2006.01)
- *C12M 1/34* (2006.01)
- *C12M 3/00* (2006.01)
- *C07H 21/02* (2006.01)
- *C07H 21/04* (2006.01)

(52) U.S. Cl.
USPC ....... 435/6.1; 435/6.11; 435/91.1; 435/287.2; 536/23.1; 536/24.3; 536/24.33

(58) Field of Classification Search
USPC ............ 435/6, 91.1, 91.2, 183, 287.1, 287.2; 436/94, 501; 536/23.1, 24.3, 24.33, 25.3, 536/25.32

See application file for complete search history.

(56) References Cited

U.S. PATENT DOCUMENTS

| 5,445,934 | A | 8/1995 | Fodor et al. |
| 2006/0008833 | A1* | 1/2006 | Jacobson ................... 435/6 |
| 2006/0166199 | A1 | 7/2006 | Marton et al. |

FOREIGN PATENT DOCUMENTS

| KR | 1020030011152 A | 2/2003 |
| KR | 1020030072883 A | 9/2003 |
| KR | 1020040076201 A | 8/2004 |

OTHER PUBLICATIONS

The definition of "correspond". Printed on Sep. 30, 2011.*
Pease et al. "Light-Generated Oligonucleotide Arrays for Rapid DNA Sequence Analysis," *Proc. Natl. acad. Sci.*, 91: 5022-5026 (1994).

* cited by examiner

*Primary Examiner* — Frank Lu
(74) *Attorney, Agent, or Firm* — Leydig, Voit & Mayer, Ltd.

(57) ABSTRACT

Provided are a method of analyzing a sequence of a first probe nucleic acid using a substrate on which a second probe nucleic acid is immobilized, and a microarray and a kit for the same.

7 Claims, 2 Drawing Sheets

SEQUENCE LISTING

<160> NUMBER OF SEQ ID NOS: 18

<210> SEQ ID NO 1
<211> LENGTH: 19

```
<212> TYPE: DNA
<213> ORGANISM: Artificial Sequence
<220> FEATURE:
<223> OTHER INFORMATION: 2nd probe nucleic acid

<400> SEQUENCE: 1
cagctatcaa ctcgcgccc                                                  19

<210> SEQ ID NO 2
<211> LENGTH: 19
<212> TYPE: DNA
<213> ORGANISM: Artificial Sequence
<220> FEATURE:
<223> OTHER INFORMATION: 2nd target nucleic acid

<400> SEQUENCE: 2
gagttgatag ctggctggt                                                  19

<210> SEQ ID NO 3
<211> LENGTH: 25
<212> TYPE: DNA
<213> ORGANISM: Artificial Sequence
<220> FEATURE:
<223> OTHER INFORMATION: 2nd target nucleic acid

<400> SEQUENCE: 3
gggcgcgagt tgatagctgg ctggt                                           25

<210> SEQ ID NO 4
<211> LENGTH: 25
<212> TYPE: DNA
<213> ORGANISM: Artificial Sequence
<220> FEATURE:
<223> OTHER INFORMATION: 2nd probe nucleic acid

<400> SEQUENCE: 4
accagccagc tatcaactcg cgccc                                           25

<210> SEQ ID NO 5
<211> LENGTH: 25
<212> TYPE: DNA
<213> ORGANISM: Artificial Sequence
<220> FEATURE:
<223> OTHER INFORMATION: 2nd target nucleic acid

<400> SEQUENCE: 5
tctacacctg cggtgctaac cagcg                                           25

<210> SEQ ID NO 6
<211> LENGTH: 25
<212> TYPE: DNA
<213> ORGANISM: Artificial Sequence
<220> FEATURE:
<223> OTHER INFORMATION: 2nd probe nucleic acid

<400> SEQUENCE: 6
cgctggttag caccgcaggt gtaga                                           25

<210> SEQ ID NO 7
<211> LENGTH: 25
<212> TYPE: DNA
<213> ORGANISM: Artificial Sequence
<220> FEATURE:
<223> OTHER INFORMATION: 2nd target nucleic acid

<400> SEQUENCE: 7
cgccgtaaat caatcgatga gttgc                                           25
```

<210> SEQ ID NO 8
<211> LENGTH: 25
<212> TYPE: DNA
<213> ORGANISM: Artificial Sequence
<220> FEATURE:
<223> OTHER INFORMATION: 2nd probe nucleic acid

<400> SEQUENCE: 8
gcaactcatc gattgattta cggcg                                          25

<210> SEQ ID NO 9
<211> LENGTH: 25
<212> TYPE: DNA
<213> ORGANISM: Artificial Sequence
<220> FEATURE:
<223> OTHER INFORMATION: 2nd target nucleic acid

<400> SEQUENCE: 9
gagacggaaa tccatcgctc gacca                                          25

<210> SEQ ID NO 10
<211> LENGTH: 25
<212> TYPE: DNA
<213> ORGANISM: Artificial Sequence
<220> FEATURE:
<223> OTHER INFORMATION: 2nd probe nucleic acid

<400> SEQUENCE: 10
tggtcgagcg atggatttcc gtctc                                          25

<210> SEQ ID NO 11
<211> LENGTH: 25
<212> TYPE: DNA
<213> ORGANISM: Artificial Sequence
<220> FEATURE:
<223> OTHER INFORMATION: 2nd target nucleic acid

<400> SEQUENCE: 11
tctcgcgcgg ctccgacacg ggcac                                          25

<210> SEQ ID NO 12
<211> LENGTH: 25
<212> TYPE: DNA
<213> ORGANISM: Artificial Sequence
<220> FEATURE:
<223> OTHER INFORMATION: 2nd probe nucleic acid

<400> SEQUENCE: 12
gtgcccgtgt cggagccgcg cgaga                                          25

<210> SEQ ID NO 13
<211> LENGTH: 25
<212> TYPE: DNA
<213> ORGANISM: Artificial Sequence
<220> FEATURE:
<223> OTHER INFORMATION: 2nd target nucleic acid

<400> SEQUENCE: 13
gacacgggca ctgtgtccag accag                                          25

<210> SEQ ID NO 14
<211> LENGTH: 25
<212> TYPE: DNA
<213> ORGANISM: Artificial Sequence
<220> FEATURE:
<223> OTHER INFORMATION: 2nd probe nucleic acid

```
<400> SEQUENCE: 14
ctggtctgga cacagtgccc gtgtc                                              25

<210> SEQ ID NO 15
<211> LENGTH: 25
<212> TYPE: DNA
<213> ORGANISM: Artificial Sequence
<220> FEATURE:
<223> OTHER INFORMATION: 2nd target nucleic acid

<400> SEQUENCE: 15
ccagccacca gcttgcatga tctcc                                              25

<210> SEQ ID NO 16
<211> LENGTH: 25
<212> TYPE: DNA
<213> ORGANISM: Artificial Sequence
<220> FEATURE:
<223> OTHER INFORMATION: 2nd probe nucleic acid

<400> SEQUENCE: 16
ggagatcatg caagctggtg gctgg                                              25

<210> SEQ ID NO 17
<211> LENGTH: 25
<212> TYPE: DNA
<213> ORGANISM: Artificial Sequence
<220> FEATURE:
<223> OTHER INFORMATION: 2nd target nucleic acid

<400> SEQUENCE: 17
agaccaggcc aggtatctct gacca                                              25

<210> SEQ ID NO 18
<211> LENGTH: 25
<212> TYPE: DNA
<213> ORGANISM: Artificial Sequence
<220> FEATURE:
<223> OTHER INFORMATION: 2nd probe nucleic acid

<400> SEQUENCE: 18
tggtcagaga tacctggcct ggtct                                              25
```

METHOD OF ANALYZING PROBE NUCLEIC ACID, MICROARRAY AND KIT FOR THE SAME

CROSS-REFERENCE TO RELATED APPLICATIONS

This application claims priority to Korean Patent Application No. 10-2009-0006261, filed on Jan. 23, 2009, and all the benefits accruing thereform under 35 U.S.C. §119, the content of which in its entirety is herein incorporated by reference.

BACKGROUND

1. Field

One or more exemplary embodiments of the present invention relate to a method of analyzing a sequence of a probe nucleic acid immobilized on a substrate, a microarray and a kit for the same.

2. Description of the Related Art

Generally, in a typical microarray, probe materials that bind to a target material are immobilized to a plurality of distinct regions of a substrate. The microarray is used in analyzing many target materials by contacting a sample, possibly including the target material labeled with a fluorescent material, with the probe materials on the microarray, and measuring light obtained therefrom. Since the regions (hereinafter also referred to as spots) of the microarray where probe materials are immobilized are generally arranged to have a high density on the microarray, the number of irradiated and detected spots used in one experiment may be thousands to tens of thousands; in other words, a single microarray may contain thousands, or more, of individual regions disposed thereon.

A nucleic acid microarray generally has a substrate on which regions having probe nucleic acids immobilized through the 3' or 5' end of the probe nucleic acids are arranged. The regions are densely arranged on the substrate. For example, the regions may be arranged on the substrate with a density equal to or more than $400/cm^2$, equal to or more than $10^3/cm^2$ or equal to or more than $10^4/cm^2$. The probe nucleic acids may be synthesized in situ on the substrate by photolithography, or synthesized in a liquid or solid phase and immobilized on the substrate by spotting. In situ synthesis refers to a continuous elongation of a nucleotide or oligonucleotide.

Typical method for identifying the sequence or length of probe nucleic acids synthesized or immobilized on a substrate of a microarray include, for example separating the probe nucleic acids from the substrate, and identifying a sequence or length of the separated nucleic acids. The nucleic acid sequence may be analyzed by sequencing and mass spectrometry. However, since a variety of types of probe nucleic acids may be immobilized on a substrate of a microarray, it is difficult to simultaneously identify the sequence and/or length of the probe nucleic acids.

Thus, there is still a need to develop a method of efficiently identifying information of probe nucleic acids immobilized on a substrate.

SUMMARY

One or more exemplary embodiments of the present invention include a method of efficiently analyzing a sequence of a probe nucleic acid immobilized on a substrate.

One or more exemplary embodiments of the present invention include a microarray for efficiently analyzing a sequence of a probe nucleic acid.

One or more exemplary embodiments of the present invention include a kit for analyzing a sequence of a probe nucleic acid of a microarray.

According to one or more exemplary embodiments of the present invention, a method of analyzing a sequence of a probe nucleic acid immobilized on a substrate includes: preparing a substrate on which a first probe nucleic acid and a second probe nucleic acid are immobilized on distinct regions, wherein the sequence of the first probe nucleic acid is synthesized and immobilized on the substrate in the same manner used to synthesize and immobilize the second probe nucleic acid, wherein the second probe nucleic acid has a sequence different from that of the first probe nucleic acid and comprises at least one nucleic acid having a length ranging from 6 nt to n nt, wherein the n nt is a length of the first probe nucleic acid; hybridizing a second target nucleic acid, which is labeled with a detectable signal substance and is complementary to the second probe nucleic acid, with the second probe nucleic acid; determining a hybridized region between the second probe nucleic acid and the second target nucleic acid by measuring a signal from the hybridized product and comparing the measured signal with reference signals; and determining that a region of the first probe nucleic acid corresponding to the hybridized region is prepared as designed.

According to one or more exemplary embodiments of the present invention, a microarray includes a substrate on which a first probe nucleic acid and a second probe nucleic acid are immobilized on distinct regions, wherein the second probe nucleic acid has a sequence different from that of the first probe nucleic acid and comprises at least one nucleic acid having a length ranging from 6 nt to n nt, wherein the n nt is a length of the first probe nucleic acid.

According to one or more exemplary embodiments of the present invention, a kit for analyzing a sequence of a probe nucleic acid of a microarray includes the microarray mentioned above.

Additional aspects will be set forth in part in the description which follows and, in part, will be apparent from the description, or may be learned by practice of the presented embodiments.

BRIEF DESCRIPTION OF THE DRAWINGS

These above and other aspects, advantages, and features of this disclosure will become more apparent and more readily appreciated from the following description of the exemplary embodiments, taken in conjunction with the accompanying drawings of which.

DETAILED DESCRIPTION

Figure 1:
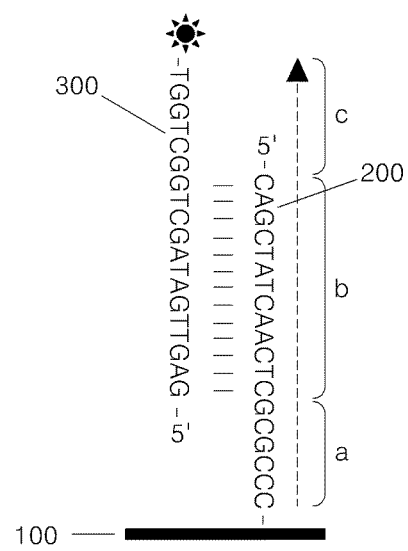
FIG. 1 is a diagram illustrating an exemplary embodiment of hybridization of a second target nucleic acid (sequence 300 on left; SEQ ID NO: 2) and a second probe nucleic acid (sequence 200 on right; SEQ ID NO: 1) immobilized on a substrate 100.

The invention is described more fully hereinafter with reference to the accompanying drawings, in which exemplary embodiments of the invention are shown. This invention may, however, be embodied in many different forms and should not be construed as limited to the exemplary embodiments set forth herein. Rather, these embodiments are provided so that this disclosure will be thorough and complete, and will fully convey the scope of the invention to those skilled in the art.

It will be understood that when an element is referred to as being "on" or "connected to" another element, the element can be directly on or connected to another element or intervening elements. In contrast, when an element is referred to as being "directly on" or "directly connected to" another element, there are no intervening elements present. As used herein, the term "and/or" includes any and all combinations of one or more of the associated listed items.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer, or section from another region, layer or section. Thus, a first element, component, region, layer, or section discussed below could be termed a second element, component, region, layer, or section without departing from the teachings of the disclosure.

The terminology used herein is for the purpose of describing particular embodiments only and is not intended to be limiting of the invention. As used herein, the singular forms "a", "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

Hereinafter, reference will now be made in detail to embodiments, examples of which are illustrated in the accompanying drawings.

In one embodiment, a method of analyzing a sequence of a probe nucleic acid immobilized on a substrate includes: preparing a substrate on which a first probe nucleic acid and a second probe nucleic acid are immobilized on distinct regions, wherein the sequence of the first probe nucleic acid is synthesized and immobilized on the substrate in the same manner used to synthesize and immobilize the second probe nucleic acid, and wherein the second probe nucleic acid has a sequence different from that of the first probe nucleic acid and includes at least one nucleic acid having a length ranging from 6 nucleotides (nt) to n nt, wherein the n nt is a length of the first probe nucleic acid; hybridizing a second target nucleic acid, which is labeled with a detectable signal substance and is complementary to the second probe nucleic acid, to the second probe nucleic acid; determining a hybridized region between the second probe nucleic acid and the second target nucleic acid by measuring a signal from the hybridized product and comparing the measured signal with reference signals; and determining that a region of the first probe nucleic acid corresponding to the hybridized region is prepared as designed.

The method includes preparing a substrate on which a first probe nucleic acid and a second probe nucleic acid are immobilized on distinct regions, wherein the second probe nucleic acid has a sequence different from that of the first probe nucleic acid and includes at least one nucleic acid having a length ranging from 6 nt to n nt, wherein the n nt is a length of the first probe nucleic acid.

The first and second probe nucleic acids may be DNA, RNA, or PNA. The first probe nucleic acid and the second probe nucleic acid may be synthesized on the substrate using the same process. The process of synthesizing nucleic acids on a substrate is known in the art. For example, the first probe nucleic acid and the second probe nucleic acid may be synthesized by repeating elongation of a nucleotide or oligonucleotide using photolithography. For example, the synthesis of the nucleic acids having a desired sequence using photolithography may be performed by irradiating light on a substrate surface-treated with functional groups removable by light through a mask to deprotect and activate a region of the surface, elongating a first nucleotide or a first oligonucleotide from the deprotected and activated region of the substrate by contacting the first nucleotide or the first oligonucleotide protected by functional groups removable by light, and repeating the deprotection and activation process by light and the elongation process using a second nucleotide or a second oligonucleotide.

In one embodiment, the first probe nucleic acid is immobilized on the substrate to identify a sequence of a first target nucleic acid. The first probe nucleic acid may not have a sequence having 4 or more of the same nucleotides in series. The first probe nucleic acid may have a sequence specifically complementary to the sequence of the first target nucleic acid to be analyzed in a sample. The second probe nucleic acid sequence is used to analyze the sequence of the first probe nucleic acid. The sequence of the second probe nucleic acid is different from that of the first probe sequence. However, the second probe nucleic acid has a region corresponding to that of the first probe sequence in terms of location from the substrate. The first probe sequence may be analyzed by analyzing the second probe sequence and using the analyzed data from the second probe sequence as being correspondingly the same with respect to the first probe sequence. For example, the first target nucleic acid, to be analyzed using the first probe sequence, may not include the sequence of the second probe nucleic acid. For example, the biological origin of the first target nucleic acid may be different from the biological origin of the second probe nucleic acid, such the first target nucleic acid and second probe nucleic acids are derived from different species, family, order, class, phylum, or kingdom. The second probe nucleic acid may also have a low sequence homology with the first probe nucleic acid. Low sequence homology refers to a degree of sequence homology by which the second probe nucleic acid is not hybridized with the first probe nucleic acid under conditions for the hybridization of the second probe nucleic acid and the second target nucleic acid. The low sequence homology may be selected by those of ordinary skill in the art. Even though the sequence of the second probe nucleic acid is different from that of the first probe sequence, the second probe nucleic acid may have a region corresponding to that of the first probe sequence in terms of location from the substrate. When the first probe sequence and the second probe sequence are synthesized on the substrate in the same manner, for example, by a method synthesizing one nucleotide or oligonucleotide by one nucleotide or oligonucleotide on the substrate including a photolithography, the first probe sequence may be analyzed by analyzing the second probe sequence and using the analyzed data from the second probe sequence as being correspondingly the same with respect to the first probe sequence. In this manner, the first probe sequence, for example, its exactness of nucleotide sequence, may be analyzed by analyzing the sequence of the second probe sequence.

In an embodiment, the second probe nucleic acid may be a set of nucleic acids having lengths ranging from 6 nt to n nt, and each of the second probe nucleic acids may be immobilized on distinct regions. That is, a set of nucleic acids having a maximum length of n nt, e.g. having lengths of 6 nt, 7 nt, and 8 nt, is immobilized on distinct regions, wherein the n nt is the length of the first probe nucleic acid. Each distinct region may contain one type of nucleic acids having specific sequence and length. Each set immobilized on distinct regions may have the same nucleotide sequence or have different nucleotide sequences compared with other immobilized sets.

According to one embodiment, the first and second probe nucleic acids may have the 3' end immobilized on the substrate and the 5' end exposed. In an alternative embodiment, the first and second probe nucleic acids may have the 5' end immobilized on the substrate, and the 3' end exposed. The length of the first and second probe nucleic acids may be in the range of 6 to 200 nt. The length of the first and second probe nucleic acids may be in the range of 6 to 100 nt. The length of the first and second probe nucleic acids may be in the range of 6 to 50 nt. The length of the first and second probe nucleic acids may be in the range of 6 to 30 nt. The length of the first and second probe nucleic acids may be in the range of 6 to 20 nt. The length of the first and second probe nucleic acids may be in the range of 6 to 15 nt. The length of the first and second probe nucleic acids may be in the range of 10 to 30 nt. The length of the first and second probe nucleic acids may be in the range of 10 to 20 nt. The length of the first and second probe nucleic acids may be in the range of 15 to 30 nt.

In one embodiment, the substrate may be selected from the group consisting of a glass substrate, a silicon substrate, and a plastic substrate. The substrate may be a microarray having a plurality of regions. A microarray is a substrate on which regions having probe nucleic acids immobilized through the 3' or 5' end of the probe nucleic acids are arranged, and are well known in the art. The regions are densely arranged on the substrate. For example, the regions may be arranged on the substrate with a density equal to or more than $400/cm^2$, equal to or more than $10^3/cm^2$ or equal to or more than $10^4/cm^2$. Distinct regions on the microarray substrate refer to regions distinguished from each other regardless of the shape and size of the regions. A dimension of the cross-section of the regions may be in the range of about 1 nm to about 5 μm, for example, about 1 nm to about 4 μm. The dimension of the cross-section may be a diameter for a circular cross-section or a length of a line going through the center of gravity of the cross-section of a region if the region has a shape other than a circle.

In one embodiment, the method includes hybridizing a second target nucleic acid, which is labeled with a detectable signal substance and is complementary to the second probe nucleic acid, with the second probe nucleic acid.

The hybridizing the second target nucleic acid with the second probe nucleic acid may be performed using a known method. For example, according to a general method, the target nucleic acid may be denatured, and the denatured target nucleic acid may be annealed to the probe nucleic acid. The denaturation may be thermal denaturation. The annealing may be performed in a hybridization buffer, e.g., SSC and SSPE. For example, the hybridization of a nucleic acid probe and a target nucleic acid may be performed by mixing the target nucleic acid labeled with a fluorescent marker with a hybridization buffer, denaturing the target nucleic acid by heat-treatment, adding the solution to a microarray, covering the microarray, and maintaining the resultant at a temperature at which the resultant is not dried. Thus, a hybrid is formed. Then, the unbound or nonspecifically bound substances may be removed by washing using a solution having a controlled salt concentration and temperature. The second target nucleic acid may be genome DNA, fragments thereof, cDNA, or products amplified by polymerase chain reaction (PCR).

In one embodiment, the second target nucleic acid is labeled with a detectable signal substance. The detectable signal substance may be a luminescence substance, a radioactive substance, or an electrical substance. For example, the detectable signal substance may be a fluorescent substance. The fluorescent substance may include at least one of the groups consisting of fluorescein, rhodamine, cyanines including Cy3 and Cy5, and metalloporphyrin complex. The fluoresein dye may be 6-carboxyl-fluorescein (6-FAM) 1,2',4',1,4,-tetrachlorofluorescein (TET) and 2',4',5',7',1,4-hexachlorofluorescein (HEX), 2',7'-dimethoxy-4',5'-dichloro-6-carboxyrhodamine (JOE), 2'-chloro-5'-fluoro-7',8'-fused phenyl-1,4-dichloro-6-carboxyfluorescein, and 2'-chloro-7'-phenyl-1,4-dichloro-6-carboxyfluorescein. The fluorescein and rhodamine dyes may have 1,4-dichloro group. The detectable signal substance may be connected to the 3' end, 5' end or both ends of the second target nucleic acid. The detectable signal substance may be connected via —OH group of the 3' end or 5' end, but is not limited thereto.

In one embodiment, the second target nucleic acid may be a nucleic acid having a length ranging from 13 nt to n nt and having a sequence complementary to 6 nt or more of the second probe nucleic acid from the distal end of the second probe nucleic acid, wherein the n nt is the length of the first probe nucleic acid. The length of the second target nucleic acid may be in the range of 13 to 200 nt. The length of the second target nucleic acid may be in the range of 13 to 100 nt. The length of the second target nucleic acid may be in the range of 13 to 50 nt. The length of the second target nucleic acid may be in the range of 13 to 30 nt. The length of the second target nucleic acid may be in the range of 13 to 20 nt. The length of the second target nucleic acid may be in the range of 13 to 30 nt. The length of the second target nucleic acid may be in the range of 13 to 20 nt. The length of the second target nucleic acid may be in the range of or 13 to 30 nt.

Since the second target nucleic acid has a sequence complementary to 6 nt or more of the second probe nucleic acid from the distal end of the second probe nucleic acid, a sequence equal to or greater than 6 nt from the distal end of the second probe nucleic acid immobilized on the substrate may be identified based on the results of the hybridization of the second target nucleic acid and the second probe nucleic acid.

In one embodiment, the first target nucleic acid is labeled with a detectable signal substance, wherein the detectable signal substance is as discussed above.

In one embodiment, the method includes determining a hybridized region between the second probe nucleic acid and the second target nucleic acid by measuring a signal from the hybridized product and comparing the measured signal with reference signals.

In the determining the hybridized region, the reference signals may be obtained by hybridizing the second probe nucleic acid and the second target nucleic acid having a known complementary nucleotide sequences or by hybridizing the first probe nucleic acid and the first target nucleic acid having a known complementary nucleotide sequences.

The determining the hybridized region may further comprise determining the length of the hybridized region. The length of the hybridized region may be easily derived by an ordinary skill in the art since the complementary nucleotide sequences are known. The determining the hybridized region may further comprise comparing the measured signal with negative control signal. The negative control signal may be signal from a hybridization between the first or the second target nucleic acid and microarray without having any immobilized probe nucleic acid. The hybridized region having one or more complementary nucleotides, for example, 6 or more complementary nucleotides may give a signal intensity greater than the negative control signal.

In one embodiment, the method also includes determining that a region of the first probe nucleic acid corresponding to the hybridized region is prepared as designed. The sequence on a region of the first probe nucleic acid corresponding to the hybridized region in terms of a location from the substrate may be indirectly estimated to be correctly prepared or synthesized since the first probe nucleic acid and the second probe nucleic acid were prepared in a same process and thus, reaction error during the preparation thereof may be equivalently occurred. However, the one or more embodiment of the present invention does not limited to a specific action mechanism.

In another embodiment, a microarray includes a substrate on which a first probe nucleic acid and a second probe nucleic acid are immobilized on distinct regions, wherein the second probe nucleic acid has a sequence different from that of the first probe nucleic acid and includes at least one nucleic acid having a length ranging from 6 nt to n nt, wherein the n nt is a length of the first probe nucleic acid.

The substrate is described above. The first probe nucleic acid, the second probe nucleic acid, and the second target nucleic acid are also described above. The first probe nucleic acid and the second probe nucleic acid may be simultaneously synthesized by repeating elongation of a nucleotide or oligonucleotide using photolithography. The second probe nucleic acid may be a set of nucleic acids having lengths ranging from 6 nt to n nt, wherein the n nt is a length of the first probe nucleic acid, and each of the second probe nucleic acids is immobilized on distinct regions.

In another embodiment, a kit for analyzing a sequence of a probe nucleic acid of a microarray comprises the microarray described above. The kit may include a second target nucleic acid labeled with a detectable marker. The second target nucleic acid labeled with the detectable marker is described above. The kit may further include a manual explaining how to use the kit according to the method of analyzing the sequence of the probe nucleic acid immobilized on a substrate of the microarray.

Hereinafter, one or more embodiments of the present invention will be described in detail with reference to the following examples. However, these examples are not intended to limit the purpose and scope of the one or more embodiments of the present invention.

Example 1

Preparation of Microarray Immobilized with Second Probe Nucleic Acid Set

A length of a first probe nucleic acid to be synthesized in a region of a substrate was set to 25 nt, and a second probe nucleic acid for analyzing the sequence of the first probe nucleic acid was prepared and immobilized on another region of the substrate. The first and second probe nucleic acids were synthesized by repeating elongation of a nucleotide using photolithography.

(1) Preparation of Second Probe Nucleic Acid

For this example, a human originated first target nucleic acid was used. For this example, 8 types of nucleic acids having a length of 25 nt were selected from a virus having a sequence with low homology compared to that of humans, i.e., from Cre recombinase gene of *Enterobacteria* phage P1, as a second target nucleic acid. Then, a sequence that is complementary to that of the second target nucleic acid and has a length ranging from 6 nt to 25 nt was selected as a second probe nucleic acid.

The 8 selected second target nucleic acids having a length of 25 nt and the corresponding 8 second probe nucleic acids having a length of 25 nt had sequences as shown in Table 1 below.

TABLE 1

| No. | Second target nucleic acid | Second probe nucleic acid | Length | Tm | Origin |
|---|---|---|---|---|---|
| 1 | SEQ ID NO: 3 | SEQ ID NO: 4 | 25 | 82 | Enterobacteria phage P1 |
| 2 | SEQ ID NO: 5 | SEQ ID NO: 6 | 25 | 80 | Enterobacteria phage P1 |
| 3 | SEQ ID NO: 7 | SEQ ID NO: 8 | 25 | 74 | Enterobacteria phage P1 |
| 4 | SEQ ID NO: 9 | SEQ ID NO: 10 | 25 | 78 | Enterobacteria phage P1 |
| 5 | SEQ ID NO: 11 | SEQ ID NO: 12 | 25 | 88 | Enterobacteria phage P1 |
| 6 | SEQ ID NO: 13 | SEQ ID NO: 14 | 25 | 82 | Enterobacteria phage P1 |
| 7 | SEQ ID NO: 15 | SEQ ID NO: 16 | 25 | 80 | Enterobacteria phage P1 |
| 8 | SEQ ID NO: 17 | SEQ ID NO: 18 | 25 | 78 | Enterobacteria phage P1 |

The second target nucleic acids or the second probe nucleic acid had 70% or less sequence homology with the human genome. For the second target nucleic acids or the second probe nucleic acid the same nucleotide was not repeated consecutively more than three times, and the second target nucleic acids and the second probe nucleic acid had a GC % ranging from about 56% to about 76%.

Twenty (20) second probe nucleic acids having contiguous sequences having lengths ranging from 6 nt to 25 nt from the 3' end of the second probe nucleic acid sequences shown in Table 1 were selected. In addition, five (5) second target nucleic acids having contiguous sequences having lengths of 13 nt, 16 nt, 19 nt, 22 nt and 25 nt from the 5' end of the second target nucleic acid sequences shown in Table 1 were selected.

As a result, 40 types of the second target nucleic acids (8 types×5 lengths) and 160 types of the second probe nucleic acid (8 types×20 lengths) were designed.

(2) Immobilization of Second Probe Nucleic Acid on Substrate

The prepared 160 types of the second probe nucleic acids were respectively immobilized on distinct regions in 60 times. The second probe nucleic acids were immobilized on the surface of the substrate by synthesizing the probe in situ on the surface of the substrate. The probe synthesis was performed using deoxyribonucleoside 3'-phosphoamidites as an activated monomer. First, a —OH group was introduced to the substrate. Then, the —OH group was reacted with deoxyribonucleoside-3'-phosphoamidite of 4 types of monomers having a dimethoxytrityl (DMT) group at 5' oxygen, β-cyanoethyl protecting group and diisopropylamino protecting group at 3'-phosphoryl oxygen, and a protecting group at pyrimidine and purine amino groups, i.e., adenine, thymine, guanine, and cytosine, to elongate nucleotides one by one. Using photolithography, the probe was selectively synthesized on the regions. The synthesis of the probe was performed in the 3'→5' direction.

A part of arrangement of the second probe nucleic acids immobilized on the substrate is shown in Table 2 below.

TABLE 2

| Probe | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| 1 | 6 | 7 | 8 | 9 | 10 | 11 | 12 | 13 | 14 | 15 | 16 | 17 | 18 | 19 | 20 | 21 | 22 | 23 | 24 | 25 |
| 2 | 6 | 7 | 8 | 9 | 10 | 11 | 12 | 13 | 14 | 15 | 16 | 17 | 18 | 19 | 20 | 21 | 22 | 23 | 24 | 25 |
| 3 | 6 | 7 | 8 | 9 | 10 | 11 | 12 | 13 | 14 | 15 | 16 | 17 | 18 | 19 | 20 | 21 | 22 | 23 | 24 | 25 |
| 4 | 6 | 7 | 8 | 9 | 10 | 11 | 12 | 13 | 14 | 15 | 16 | 17 | 18 | 19 | 20 | 21 | 22 | 23 | 24 | 25 |
| 5 | 6 | 7 | 8 | 9 | 10 | 11 | 12 | 13 | 14 | 15 | 16 | 17 | 18 | 19 | 20 | 21 | 22 | 23 | 24 | 25 |
| 6 | 6 | 7 | 8 | 9 | 10 | 11 | 12 | 13 | 14 | 15 | 16 | 17 | 18 | 19 | 20 | 21 | 22 | 23 | 24 | 25 |
| 7 | 6 | 7 | 8 | 9 | 10 | 11 | 12 | 13 | 14 | 15 | 16 | 17 | 18 | 19 | 20 | 21 | 22 | 23 | 24 | 25 |
| 8 | 6 | 7 | 8 | 9 | 10 | 11 | 12 | 13 | 14 | 15 | 16 | 17 | 18 | 19 | 20 | 21 | 22 | 23 | 24 | 25 |

Referring to Table 2, each column indicates the length of the probe, and each row indicates the 8 types of second probe nucleic acids having different lengths, i.e., lengths ranging from 6 nt to 25 nt. The probe nucleic acids in the each row have a common sequence of 6 nt length and increase by one nucleotide at the 5' end up to 25 nucleotides. Referring to the probe nucleic acids in the second row as an example, the probe consists of p(1,1), p(1,2), p(1,3)..., and p(1,25). P(1,2) differs from one nucleotide from p(1,1) and p(1,2) has one more nucleotide at the 5' end compared to p(1,1). P(1,3) differs from one nucleotide from p(1,2) and p(1,3) has one more nucleotide at the 5' end compared to p(1,2). In the same way, p(1,25) differs from one nucleotide from p(1,24) and p(1,25) has one more nucleotide at the 5' end compared to p(1,24).

FIG. 1 is a diagram illustrating hybridization of a second target nucleic acid with a second probe nucleic acid immobilized on a substrate according to an embodiment of the present invention. Referring to FIG. 1, a second probe nucleic acid (SEQ ID NO: 1) 200 is immobilized on a substrate 100 via the 3'-OH, and the 5'-OH is the distal end from the substrate. The second probe nucleic acid has a length of 19 nt. Even though FIG. 1 illustrates the second probe nucleic acid having a length of 19 nt, any second probe nucleic acid having a length equal to or less than the length of a first probe nucleic acid. For example, if the first probe nucleic acid has a length of 25 nt, at least one sequence having a length ranging from 6 nt to 25 nt may be immobilized as the second probe nucleic acid. For example, each of a plurality of sequences having lengths ranging from 6 nt to 25 nt may be immobilized on distinct regions. Alternatively, nucleic acids having a length of 13 nt, 19 nt, or 25 nt may be immobilized on distinct regions. A second target nucleic acid (SEQ ID NO: 2) 300 has a length of 19 nt, is labeled with a detectable marker via its 3'-OH end, and is hybridized with a portion of the second probe nucleic acid by 13 nt from the 5' end. Referring to FIG. 1, "a" indicates a proximal end of the second probe nucleic acid from the immobilized portion (6 nt) which is not hybridized with the second target nucleic acid, "b" indicates a distal end hybridized with the second target nucleic acid (19 nt), and "c" indicates a sequence (6 nt) corresponding to the sequence of the first probe nucleic acid (25 nt) which is not contained. The c region of the first probe nucleic acid may be identified using the second probe nucleic acid having a sequence including the c region, e.g., having a length ranging from 19 nt to 25 nt.

Example 2

Influence of the Length of Hybridization of Second Probe Nucleic Acid and Second Target Nucleic Acid on Hybridization Signal 5 types of second target nucleic acids, i.e., second target nucleic acids having lengths of 13 nt, 16 nt, 19 nt, 22 nt, and 25 nt, were hybridized with second probe nucleic acids corresponding to the second target nucleic acids and immobilized on a microarray prepared according to Example 1. Then, fluorescent signals were measured from the hybridized product. The second target nucleic acids having lengths of 13 nt, 16 nt, 19 nt, 22 nt, and 25 nt have common sequences of 13 nt at the 3' end. 16 nt target differs from 3 nucleotides from 13 nt target and 16 nt target has 3 more nucleotides at the 5' end compared to 13 nt target. 19 nt target differs from 3 nucleotides from 16 nt target and 19 nt target has 3 more nucleotides at the 5' end compared to 16 nt target. In the same way, 22 nt and 25 nt targets differ from 3 nucleotides from 19 nt and 22 nt targets, respectively and 22 nt and 25 nt targets have 3 more nucleotides at the 5' end compared to 22 nt and 25 nt targets, respectively.

Figure 2:
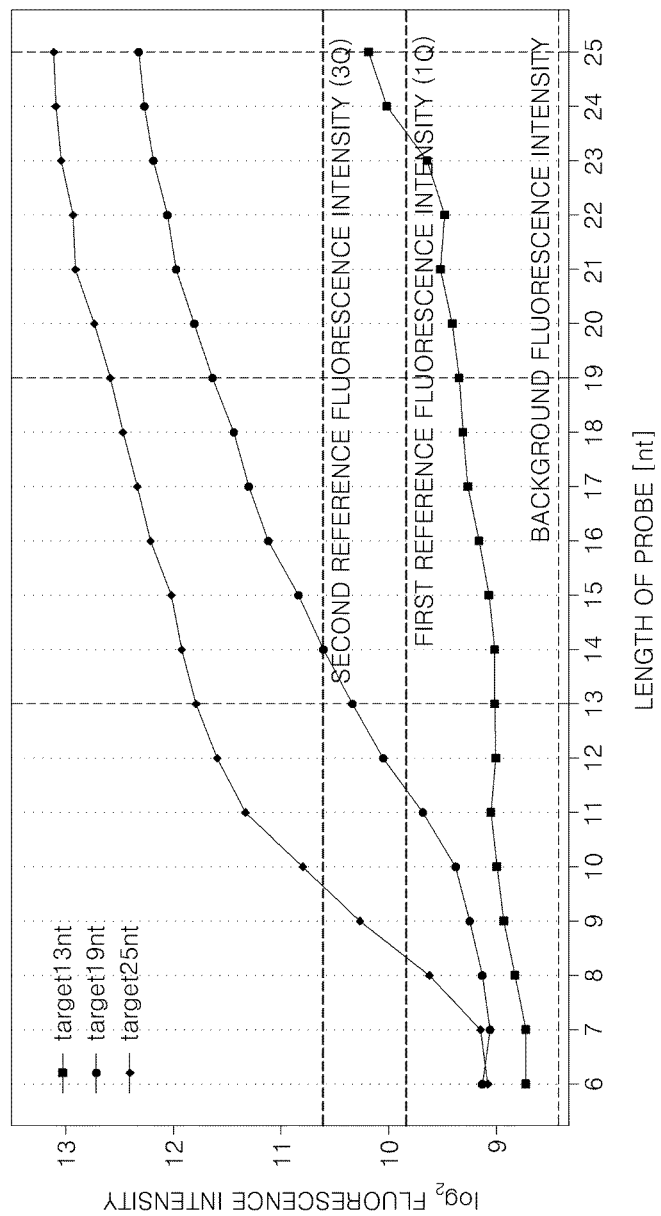
FIG. 2 is a graph illustrating log 2 fluorescence intensity versus the length of the probe (nt) of an exemplary embodiment of the intensity of hybridization according to the length of a probe in accordance with Example 2.

FIG. 2 is a graph illustrating intensity of hybridization according to the length of the probe. The x-axis indicates the length of the probe nucleic acid in nt, and the y-axis indicates the intensity of hybridization in terms of log 2 fluorescence intensity. In FIG. 2, the fluorescence intensity is an average of the measured fluorescence intensity. In FIG. 2, target 13 nt, target 19 nt, and target 25 nt indicate intensity of hybridization of the second target nucleic acids having lengths of 13 nt, 19 nt, and 25 nt and the second probe nucleic acid according to the length of the second probe nucleic acid. As shown in FIG. 2, as the length of the hybridized portion increases, the measured fluorescence intensity increases. Thus, the sequence of the second probe nucleic acid may be identified by hybridizing the second target nucleic acid having a variety of lengths with the second probe nucleic acid immobilized on the microarray. Based on the identified sequence of the second probe nucleic acid, the sequence of the first probe nucleic acid which is synthesized and immobilized on the substrate in the same manner used to synthesize and immobilize the second probe nucleic acid may be evaluated.

The accuracy of the sequence of the second probe nucleic acid may be judged as follows. In FIG. 2, the background fluorescence intensity is average fluorescence intensity when no probe nucleic acid complementarily binds to the second target nucleic acids having lengths of 13 nt, 19 nt, and 25 nt. If the second target nucleic acids are hybridized with at least one second probe nucleic acid, the fluorescence intensity is greater than the background fluorescence intensity.

In FIG. 2, the first reference fluorescence intensity refers to a fluorescence intensity obtained by hybridizing a first target nucleic acid, prepared by cleaving human genome DNA using DNaseI and labeling the 3'-OH with Cy3, with a plurality of first probe nucleic acids, having a length of 25 nt and the complementary sequence and immobilized on a microarray, measuring fluorescence intensity, and selecting a value corresponding to the bottom 25% (1Q) of the measured fluorescence intensity. The first reference fluorescence intensity may vary according to the length and type of the first probe nucleic acid. The fluorescence intensity is greater than the bottom 25%, when the first target nucleic acid is hybridized with a perfect match first probe nucleic acid (PM probe). The fluorescence intensity is less than the bottom 25%, when the first target nucleic acid is hybridized with a mismatch first probe nucleic acid (MM probe) having a single nucleotide that is not complementary to the first target nucleic acid and located at the center of the first probe nucleic acid, i.e., at the $13^{th}$ position of the first probe nucleic acid having a length of 25 nt. This reference signal value may be applied to the measured signal value obtained by hybridizing a second probe nucleic acid and a second target nucleic acid. Thus, as a result of the hybridization of the second target nucleic acid and the second probe nucleic acid, it may be determined the hybridized length of the second target nucleic acid and the second probe nucleic acid as equal to or greater than 13 nt when the measured fluorescence intensity is greater than the reference fluorescence intensity. Thus, if the fluorescence intensity is greater than the reference fluorescence intensity, when the length of hybridized sequence is greater than 13 nt in the hybridization using the second target nucleic acids having lengths of 13 nt, 19 nt, and 25 nt, it may be determined that the hybridized sequence is the desired sequence as designed. For example, if the fluorescence intensity is greater than the reference fluorescence intensity in a region in which the second probe nucleic acid having a length of 25 nt is immobilized in the hybridization using the second target nucleic acid having a length of 13 nt, it may be determined that the sequence of 13 nt from the distal end is accurate and the sequence of 13 nt from proximal end may be accurate. If the fluorescence intensity is greater than the reference fluorescence intensity in a region in which the second probe nucleic acid having a length of 19 nt is immobilized in the hybridization using the second target nucleic acid having a length of 19 nt, it may be determined that the sequence of 13 nt from the distal end is accurate and the sequence of 6 nt from proximal end may be accurate. In addition, the fluorescence intensity is greater than the reference fluorescence intensity in a region in which the second probe nucleic acid having a length of 13 nt is immobilized in the hybridization using the second target nucleic acid having a length of 25 nt, and greater than the background fluorescence intensity in a region in which the second probe nucleic acid having a length of 6 nt is immobilized, it may be determined that the sequence of 13 nt from the distal end is accurate. The sequence of 1 to 5 nt from the proximal end may be determined as accurate when the fluorescence intensity of a region in which the second probe nucleic acid having a length ranging from 20 to 25 nt is greater than a second reference fluorescence intensity when the second target nucleic acid having a length of 25 nt is used, and the fluorescence intensity of a region in which the second probe nucleic acid having a length ranging from 6 to 12 nt is greater than the background fluorescence intensity.

In FIG. 2, the second reference fluorescence intensity refers to a fluorescence intensity obtained by hybridizing a first target nucleic acid, prepared by cleaving human genome DNA using DNaseI and labeling the 3'-OH with Cy3, with a plurality of first probe nucleic acids, having a length of 25 nt and the complementary sequence and immobilized on the microarray, measuring fluorescence intensity, and selecting a value corresponding to the top 25% (3Q). The second reference fluorescence intensity may vary according to the length and type of the first probe nucleic acid. The second reference fluorescence intensity is selected from an experimental data.

According to the experimental data, when the first target nucleic acid is hybridized with a perfect match first probe nucleic acid (PM probe) immobilized on distinct regions on the surface of a substrate, the fluorescence intensity was greater than the top 25%. Further, when the first target nucleic acid is hybridized with a mismatch first probe nucleic acid (MM probe) having a single nucleotide that is not complementary to the first target nucleic acid and located at the center of the first probe nucleic acid, i.e., at the $13^{th}$ position of the first probe nucleic acid having a length of 25 nt, the fluorescence intensity is less than the top 25%. Thus, the second reference fluorescence intensity may be used as control value to determine whether a probe nucleic acid has more than 6 nt which are correctly prepared as designed from 3' end to 5' end of the probe sequences. Thus, it can be identified that a probe nucleic acid of 6 nts to 25 nts from the surface of the substrate is correctly synthesized, if a fluorescence intensity of a hybridization result between second probe and target nucleic acids is greater than the second reference fluorescence intensity.

As described above, according to the one or more of the above embodiments of the present invention, the sequence of a probe nucleic acid immobilized on a substrate may be efficiently analyzed.

The microarray according to the one or more of the above embodiments of the present invention may be used to efficiently analyze the sequence of a probe nucleic acid.

The kit according to the one or more of the above embodiments of the present invention may be used to efficiently analyze the sequence of a probe nucleic acid of a microarray.

It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. A method of estimating whether a region of a first probe nucleic acid is correctly synthesized, the method comprising:

synthesizing the first probe nucleic acid and one or more second probe nucleic acids on distinct regions of a substrate, wherein the first probe nucleic acid and the one or more second probe nucleic acids are synthesized on the substrate in the same manner, wherein the first probe nucleic acid has a length of n nucleotides (nt) and has a sequence complementary to a first target nucleic acid, and n ranges from about 10 nucleotides to about 100 nucleotides, wherein the one or more second probe nucleic acids have a sequence that is different from the sequence of the first probe nucleic acid and that is complementary to one or more second target nucleic acids, wherein the one or more second probe nucleic acids have a length ranging from 6 nucleotides to n nucleotides, wherein the first probe nucleic acid is synthesized and immobilized on the substrate in the same manner used to synthesize and immobilize the one or more second probe nucleic acids;

hybridizing the one or more second target nucleic acids with the one or more second probe nucleic acids and forming a hybridized product, wherein the one or more second target nucleic acids are labeled with a detectable signal substance;

determining a hybridized region of one of the second target nucleic acids on the hybridized product by measuring a signal generated from the detectable signal substance in said one of the second target nucleic acids on the hybridized product and comparing the signal with a reference signal, wherein the reference signal is obtained by hybridizing one of the second probe nucleic acids to one of the second target nucleic acids or hybridizing the first probe nucleic acid to the first target nucleic acid; and estimating whether the region of the first probe nucleic acid is correctly synthesized based on the results of hybridizing the one or more second target nucleic acids with the one or more second probe nucleic acids, wherein the region of the first probe nucleic acid corresponds to the hybridized region of said one of the second target nucleic acids.

2. The method of claim 1, wherein the first probe nucleic acid and the one or more second probe nucleic acids are synthesized by repeating elongation of a nucleotide or an oligonucleotide using photolithography in situ on the substrate.

3. The method of claim 1, wherein the one or more second probe nucleic acids comprises a set of probe nucleic acids, each of the probe nucleic acids in the set having a length ranging from 6 nucleotides to n nucleotides.

4. The method of claim 3, wherein said hybridizing the one or more second target nucleic acids with the one or more second probe nucleic acids comprises hybridizing a plurality of the second target nucleic acids with the one or more second probe nucleic acids, each nucleic acid in the plurality of the second target nucleic acids having a length ranging from 13 nucleotides to n nucleotides.

5. The method of claim 1, wherein said determining the hybridized region further comprises determining the length of the hybridized region.

6. The method of claim 1 wherein said determining the hybridized region further comprises comparing the signal with a negative control signal produced by hybridizing the first target nucleic acid or said one of the second nucleic acids to a microarray without any immobilized probe nucleic acid.

7. The method of claim 1, wherein the detectable signal substance is a fluorescent marker, and the signal is a fluorescence signal.

\* \* \* \* \*

UNITED STATES PATENT AND TRADEMARK OFFICE
CERTIFICATE OF CORRECTION

PATENT NO.        : 8,518,642 B2                              Page 1 of 1
APPLICATION NO.   : 12/684345
DATED             : August 27, 2013
INVENTOR(S)       : Kyung-Hee Park et al.

It is certified that error appears in the above-identified patent and that said Letters Patent is hereby corrected as shown below:

On the Title Page, after item (65) and the prior publication data, add item (30) as follows:

-- (30)     Foreign Application Priority Data
       January 23, 2009     (KR)........10-2009-0006261 --

Signed and Sealed this
Twenty-fourth Day of June, 2014

Michelle K. Lee
*Deputy Director of the United States Patent and Trademark Office*